United States Patent [19]

Miller et al.

[11] Patent Number: 5,797,847
[45] Date of Patent: Aug. 25, 1998

[54] METHOD AND APPARATUS FOR COMPLEX BANDPASS FILTERING AND DECIMATION IN ULTRASOUND BEAMFORMER

[75] Inventors: Steven C. Miller, Town of Pewaukee; Gregory A. Lillegard, Greenfield; Daniel Milon, Milwaukee, all of Wis.

[73] Assignee: General Electric Company, Milwaukee, Wis.

[21] Appl. No.: 774,666

[22] Filed: Dec. 30, 1996

[51] Int. Cl.$^6$ .................. A61B 8/00; A61N 7/00
[52] U.S. Cl. .................. 600/447; 600/443; 327/254
[58] Field of Search .................. 600/443, 453, 600/447, 555, 441, 455, 454; 375/261; 367/138, 105, 135; 342/195; 327/254

[56] References Cited

U.S. PATENT DOCUMENTS

| | | | |
|---|---|---|---|
| 5,345,426 | 9/1994 | Lipschutz | 600/447 |
| 5,345,939 | 9/1994 | Engeler et al. | 600/447 |
| 5,437,281 | 8/1995 | Lin et al. | 128/660.07 |
| 5,482,004 | 1/1996 | Lin et al. | 128/660.07 |
| 5,482,044 | 1/1996 | Lin et al. | 600/443 |
| 5,483,962 | 1/1996 | Shiba | 600/441 |
| 5,555,534 | 9/1996 | Maslak et al. | 367/135 |
| 5,581,517 | 12/1996 | Gee et al. | 367/138 |
| 5,621,345 | 4/1997 | Lee et al. | 327/254 |
| 5,685,308 | 11/1997 | Wright et al. | 600/443 |
| 5,735,797 | 4/1998 | Muzilla et al. | 600/441 |

Primary Examiner—Francis Jaworski
Assistant Examiner—Ali Imam
Attorney, Agent, or Firm—Dennis M. Flaherty; John H. Pilarski

[57] ABSTRACT

A phased array sector scanning ultrasonic system includes a separate beamformer channel for each respective element in an ultrasonic transducer array. Each beamformer channel has a three-stage complex FIR filter downstream of an analog-to-digital converter. Each filter circuit stage has a register pipeline, an in-phase FIR filter and a quadrature FIR filter. The first stage only has real samples, so there is a single pipeline. The other stages have complex inputs composed of in-phase (real) and quadrature (imaginary) samples, requiring a pipeline for each. Each register pipeline is made up of a multiplicity of registers connected in series. The number of registers in a given pipeline must equal the number of taps being used on the FIR filter immediately downstream of the register pipeline. The registers are clocked in synchronism and store successive echo data samples. Each register in the pipeline has an output connected to a respective tap of the corresponding FIR filter. In the second and third stages, the taps on the FIR filters receive data samples consisting of a real data sample from the I pipeline and/or an imaginary data sample from the Q pipeline. These complex data samples are multiplied by complex filter coefficients and the products are summed to form a respective filtered data sample output for each stage.

20 Claims, 8 Drawing Sheets

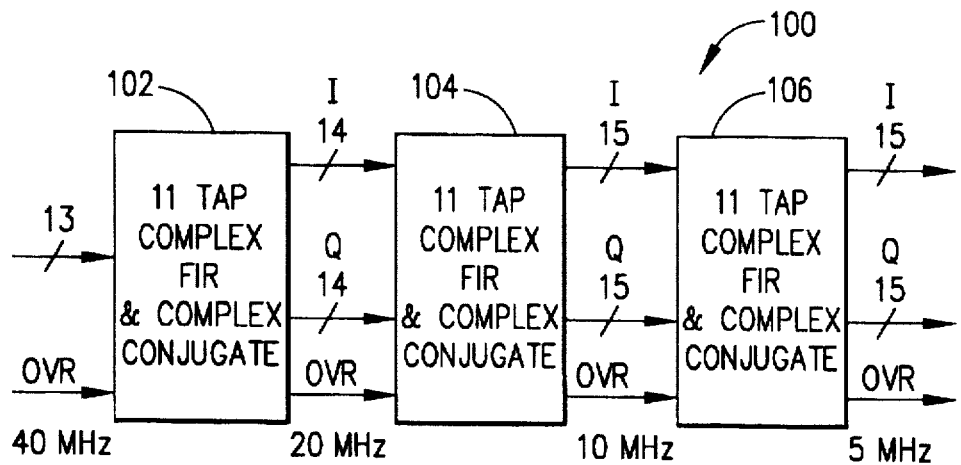
FIG. 5
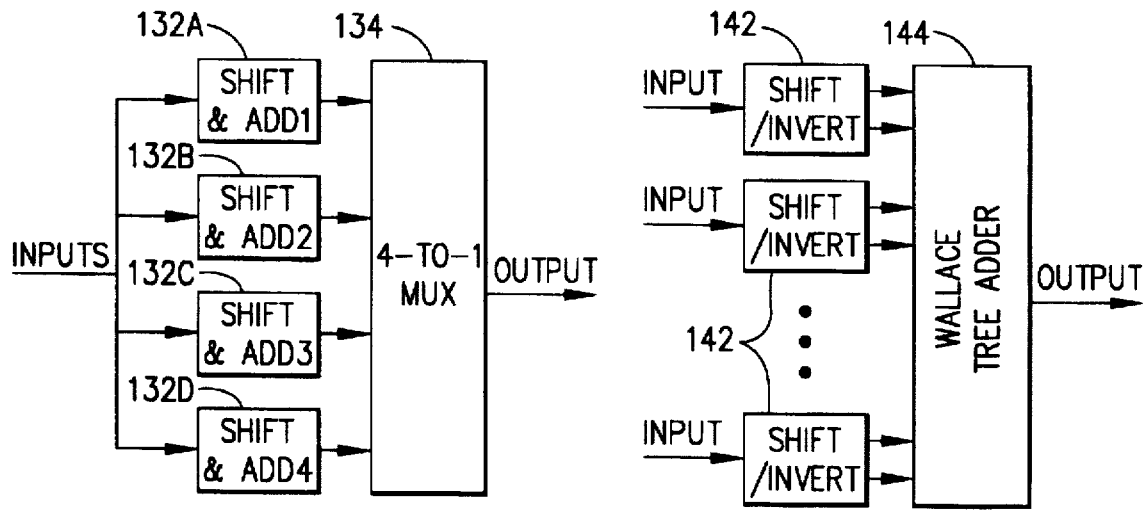
FIG. 8
FIG. 10
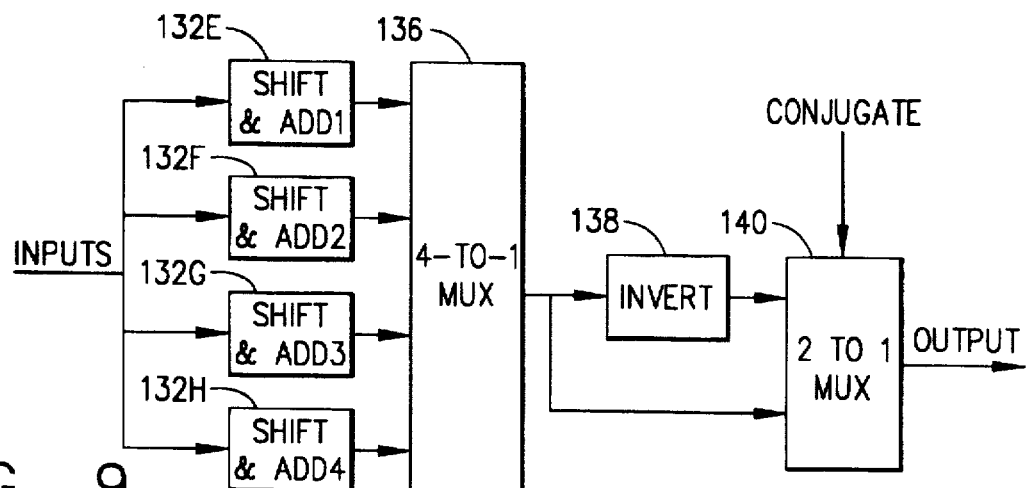
FIG. 9

METHOD AND APPARATUS FOR COMPLEX BANDPASS FILTERING AND DECIMATION IN ULTRASOUND BEAMFORMER

FIELD OF THE INVENTION

This invention generally relates to ultrasound imaging systems which form ultrasonic beams by time delay and summation of echo signals in a multiplicity of parallel channels. In particular, the invention relates to means for filtering and decimating received ultrasound echo data.

BACKGROUND OF THE INVENTION

Conventional ultrasound imaging systems comprise an array of ultrasonic transducers which are used to transmit an ultrasound beam and then receive the reflected beam from the object being studied. For ultrasound imaging, the array typically has a multiplicity of transducers arranged in a line and driven with separate voltages. By selecting the time delay (or phase) and amplitude of the applied voltages, the individual transducers can be controlled to produce ultrasonic waves which combine to form a net ultrasonic wave that travels along a preferred vector direction and is focused at a selected point along the beam. Multiple firings may be used to acquire data representing the same anatomical information. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. By changing the time delay and amplitude of the applied voltages, the beam with its focal point can be moved in a plane to scan the object.

The same principles apply when the transducer is employed to receive the reflected sound (receiver mode). The voltages produced at the receiving transducers are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer.

Such scanning comprises a series of measurements in which the steered ultrasonic wave is transmitted, and the reflected ultrasonic wave is received and stored. Typically, transmission and reception are steered in the same direction during each measurement to acquire data from a series of points along an acoustic beam or scan line. The receiver is dynamically focused at a succession of ranges along the scan line as the reflected ultrasonic waves are received.

An ultrasound image is composed of multiple image scan lines. A single scan line (or small localized group of scan lines) is acquired by transmitting focused ultrasound energy at a point in the region of interest, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. A scan line's resolution is a result of the directivity of the associated transmit and receive beam pair.

Scan lines are defined by their position and angle. The intersection of a beam with the transducer face is referred to as the phase center. The angle of a scan line relative to orthogonal is referred to as the steering angle.

Referring to FIG. 1, a conventional ultrasound imaging system includes a transducer array 10 comprised of a plurality of separately driven transducer elements 12, each of which produces a burst of ultrasonic energy when energized by a pulsed waveform produced by a transmitter 22. The ultrasonic energy reflected back to transducer array 10 from the object under study is converted to an electrical signal by each receiving transducer element 12 and applied separately to a receiver 24 through a set of transmit/receive (T/R) switches 26. The T/R switches 26 are typically diodes which protect the receive electronics from the high voltages generated by the transmit electronics. The transmit signal causes the diodes to shut off or limit the signal to the receiver. Transmitter 22 and receiver 24 are operated under control of a scan controller 28 responsive to commands by a human operator. A complete scan is performed by acquiring a series of echoes in which transmitter 22 is gated ON momentarily to energize each transducer element 12, and the subsequent echo signals produced by each transducer element 12 are applied to receiver 24. A channel may begin reception while another channel is still transmitting. The receiver 24 combines the separate echo signals from each transducer element to produce a single echo signal which is used to produce a line in an image on a display monitor 30.

Transmitter 22 drives transducer array 10 such that the ultrasonic energy produced is directed, or steered, in a beam. To accomplish this, transmitter 22 imparts a time delay to the respective pulsed waveforms W, that are applied to successive transducer elements 12 via respective beamformer channels. Each channel has a respective pulser associated therewith. By adjusting the pulse time delays appropriately in a conventional manner, the ultrasonic beam can be directed away from axis 36 by an angle θ and/or focused at a fixed range R. A sector scan is performed by progressively changing the time delays in successive excitations. The angle θ is thus changed in increments to steer the transmitted beam in a succession of directions.

The echo signals produced by each burst of ultrasonic energy reflect from objects located at successive ranges along the ultrasonic beam. The echo signals are sensed separately by each transducer element 12 and the magnitude of the echo signal at a particular point in time represents the amount of reflection occurring at a specific range. Due to the differences in the propagation paths between a reflecting point P and each transducer element 12, however, these echo signals will not be detected simultaneously and their amplitudes will not be equal. Receiver 24 amplifies the separate echo signals, imparts the proper time delay to each, and sums them to provide a single echo signal which accurately indicates the total ultrasonic energy reflected from point P located at range R along the ultrasonic beam oriented at the angle θ.

To simultaneously sum the electrical signals produced by the echoes impinging on each transducer element 12, time delays are introduced into each separate beamformer channels of receiver 24. The beam time delays for reception are the same delays as the transmission delays described above. However, the time delay of each receiver channel is continuously changing during reception of the echo to provide dynamic focusing of the received beam at the range R from which the echo signal emanates.

Under the direction of scan controller 28, receiver 24 provides delays during the scan such that steering of receiver 24 tracks the direction θ of the beam steered by transmitter 22 and provides the proper delays and phase shifts to dynamically focus at points P along the beam. Thus, each transmission of an ultrasonic pulse waveform results in the acquisition of a signal with a magnitude which represents the amount of reflected sound from anatomy located along the ultrasonic beam.

A detector 25 converts the received signal to display data. In the B-mode (greyscale), this would be the envelope of the signal with some additional processing such as edge enhancement and logarithmic compression.

Scan converter/interpolator 32 receives the display data from detector 25 and converts the data into the desired image for display. In particular, the scan converter converts the acoustic image data from polar coordinate (R-θ) sector format or Cartesian coordinate linear array to appropriately scaled Cartesian coordinate display pixel data at the video rate. This scan-converted acoustic data is then output for display on display monitor 30, which images the time-varying amplitude of the envelope of the signal as a grey scale.

Referring to FIG. 2, the receiver comprises a receive beamforming section 34 and a signal processor 38. The receive beamforming section 34 of receiver 24 includes separate beamformer channels 35. Each beamformer channel 35 receives the analog echo signal from a respective transducer element. The beamformer controller 50 converts scan line and transmit focus numbers to addresses into a channel control memory (not shown). The scan controller 28 (FIG. 2) and beamformer controller 50 (FIG. 3) are loaded by the system host CPU in response to user actions such as changing the display format or connecting a different ultrasound probe.

As seen in FIG. 3, each beamformer channel 35 comprises a receive channel and a transmit channel, each channel incorporating delay means 40 and 42 respectively, which are controlled to provide the needed beamforming delays by receive control logic 44 and transmit control logic 46 respectively. Transmit is typically done by using a counter to delay the start of transmit pulse generation. Some systems may also apply relative phase rotations in addition to, or in place of, delays for receive. The receive channels also have circuitry 48 for apodizing and filtering the receive pulses.

The signals entering the summer 36 (see FIG. 2) have been delayed so that when they are summed with delayed signals from each of the other beamformer channels 35, the summed signals indicate the magnitude and phase of the echo signal reflected from anatomy located along the steered beam (θ). Signal processor 38 receives the beam samples from the summer 36 and produces an output to scan converter 32 (see FIG. 2).

As seen in FIG. 2A, a conventional ultrasound imaging system has a beamformer wherein the processing channels 35 are separated into groups of channels mounted on separate boards, namely, beamformer (BF) boards 1–4. The output signals from the processing channels of each board are summed in a respective summer 36 located on the same board. The outputs of the four summers (only three of which appear in FIG. 2A) are in turn summed by adders 37 before being output to the signal processor.

Conventional medical ultrasound imaging equipment may receive echoes with spectral content up to 15 MHz. To sample the received signals directly, i.e., before any sort of analog demodulation or filtering, requires a sample rate of approximately 40 MHz. However, it is difficult to propagate digital data at a 40 MHz sample rate over card cage backplanes. It is preferable to downsample the data before leaving the receive board containing the analog-to-digital converters.

Some prior art digital beamformers employ analog or digital complex demodulators to mix the signal to baseband. The complex baseband data is then low-pass filtered with real-valued coefficients (not complex) and decimated (sub-sampled) to a lower data rate for propagation over the backplane. This requires generation of a very accurate local oscillator to provide the mixing signals.

As shown in FIG. 2A, the beamforming section of a conventional receiver comprises a set of signal processing channels 35—one for each element 12 of transducer 11 (see FIG. 1). As shown in FIG. 4, each signal processing channel is responsive to a START command, a 40-MHz master clock and a beam angle signal (φ) from digital scan controller 28 (see FIG. 1) to perform the digital beamforming functions. These functions include: sampling the analog input signal in an analog-to-digital converter 200; demodulating the sampled signal in a demodulator 201 to form in-phase (I) and quadrature (Q) baseband signals; filtering out the high-frequency sum signals produced by demodulator 201 with low pass filters 202; reducing the data rate in decimators 203; and time delaying and phase adjusting the resulting digital data stream in delay FIFOs (i.e., first-in/first-out memories) 204 and phase rotator 205, respectively. All of these elements are controlled by a receive channel control 206 which produces the required clock and control signals in response to commands from scan controller 28 (see FIG. 1).

Referring still to FIG. 4, analog-to-digital converter 200 samples the analog signal at regular intervals determined by the leading edge of a sample clock signal from receive channel control 206. In one conventional imaging system, the sample clock signal is a 40-MHz clock. This enables the use of ultrasonic frequencies of up to 20 MHz without violating the Nyquist sampling criteria. When a 5-MHz ultrasonic carrier frequency is employed, for example, it is sampled eight times per carrier cycle and a 10-bit digital sample is produced at the output of the analog-to-digital converter at a 40-MHz rate. These samples are supplied to demodulator 201, which mixes each sample with both a reference that is in-phase with the transmitted ultrasonic carrier and with a reference that is in quadrature with the transmitted ultrasonic carrier. The demodulator reference signals are produced from stored SINE and COSINE tables that are read out of their respective ROMs by a 40-MHz reference clock signal from receive channel control 206. The COSINE value is digitally multiplied by the sampled input signal to produce a demodulated, in-phase value (I) signal which is supplied to a low pass filter 202, and the SINE value is digitally multiplied by the same sampled input signal to produce a demodulated, quadrature phase value Q signal which is supplied to a separate low pass filter 202. Low pass filters 202 are finite impulse response filters tuned to pass the difference frequencies supplied by demodulator 201, but block the higher, sum frequencies. The output signal of each low pass filter is a stream of 40-MHz digital values which indicate the magnitude of the I or Q component of the echo signal envelope.

Referring still to FIG. 4, the rate at which the demodulated I and Q components of the echo signal are sampled is reduced by decimators 203. In a conventional system, the digital samples are supplied to the decimators at a 40-MHz rate, which is unnecessarily high from an accuracy standpoint, and which is a difficult data rate to maintain throughout the system. Accordingly, decimators 203 select every eighth digital sample to reduce the data rate down to a 5-MHz rate. This corresponds to the frequency of a baseband clock signal produced by receive channel control 206 and employed to operate the remaining elements in the receiver channel. Thus the I and Q output signals of decimators 203 are digitized samples of the echo signal envelope. The decimation ratio and the baseband clock frequency can be changed to values other than 8:1 and 5 MHz.

The echo signal envelope represented by the demodulated and decimated digital samples is then delayed by delay FIFOs 204 and phase shifted by phase rotator 205 to provide the desired beam steering and beam focusing. The I and Q outputs of phase rotator 205 are applied to the inputs of a pair of multipliers (not shown). The other input of each of the multipliers receives a window weighting factor ranging in value from 0 to 1.0 from receive channel control 206. The I and Q outputs of multipliers constitute the weighted receive channel output signals which are summed to form the receive beam.

Other prior art digital beamformers simply attempt to meet the tight tolerance required to provide 40 MHz transfer rates, or parallelize the data with two or four data busses, reducing the rate on each bus to 20 or 10 MHz, respectively. This requires a large amount of input/output hardware.

SUMMARY OF THE INVENTION

The present invention is a method and an apparatus for reducing the required data transfer across back-planes of an ultrasound imaging system without loss of information. In particular, the invention is a method and an apparatus for providing complex bandpass filtering and decimation of ultrasound echo data with minimal hardware. The preferred embodiment minimizes the amount of hardware by employing a small number of bit shifts and adds.

In accordance with the present invention, the complex bandpass filters pass only a single-sided passband of the real input decimated to a much lower rate. The frequency band of interest is thus fully represented by a minimal amount of complex data, without the need for a local oscillator.

The preferred embodiment of the complex filter is realized without multipliers. Instead, a relatively small number of bit shifts and adds are performed. The preferred embodiment uses "Wallace tree" adders to accumulate bit-shifted versions of the inputs. The number of additions is less than the number of bits which would be needed to represent equivalent coefficients. This reduces the hardware relative to a conventional implementation which incorporates multipliers with shifts and adds equaling the number of bits in the coefficients.

In accordance with the preferred embodiment of the invention, each beamformer board has a three-stage complex FIR filter circuit downstream of the processing channel summer. Each filter circuit stage has a register pipeline, an in-phase FIR filter and a quadrature FIR filter. The first stage only has real samples, so there is a single pipeline input to the FIR filters. The other stages have complex inputs composed of in-phase (real) and quadrature (imaginary) samples, requiring a pipeline for each. Each register pipeline is made up of a multiplicity of registers connected in series. The number of registers in a given pipeline must equal the number of taps being used on the FIR filter immediately downstream of the register pipeline. The registers are clocked in synchronism and store successive summed echo data samples for each beamformer board. Each register in the pipeline has an output connected to a respective tap of the corresponding FIR filter.

In the first stage, the taps on the FIR filters receive real data samples from the first-stage register pipeline. These real data samples are multiplied by real or imaginary values from a first set of complex filter coefficients and the products are summed to form first stage in-phase and quadrature filtered data sample streams having a first sampling rate. In the second stage, the taps on the FIR filters receive the in-phase and quadrature filtered data sample streams from the first stage. These data samples are multiplied by real or imaginary values from a second set of complex filter coefficients and the products are summed to form second-stage in-phase and quadrature filtered data sample streams having a second sampling rate less than the first sampling rate. In the third stage, the taps on the FIR filters receive the in-phase and quadrature filtered data sample streams from the second stage. These data samples are multiplied by real or imaginary values from a third set of complex filter coefficients and the products are summed to form third-stage in-phase and quadrature filtered data sample streams having a third sampling rate less than the second sampling rate. In accordance with the invention, the multiplication of a data sample by a coefficient is performed by bit shifting and/or inversion.

BRIEF DESCRIPTION OF THE DRAWINGS

FIG. 5 is a block diagram of a three-stage complex bandpass decimation filter in accordance with the present invention.

FIG. 8 is a block diagram of an in-phase FIR filter incorporated in each stage of the complex FIR filter circuit depicted in FIG. 6.

FIG. 9 is a block diagram of a quadrature FIR filter incorporated in each stage of the complex FIR filter circuit depicted in FIG. 6.

FIG. 10 is a block diagram showing further details of a representative shift and add block incorporated in the filters depicted in FIGS. 8 and 9.

DETAILED DESCRIPTION OF THE PREFERRED EMBODIMENTS

Figure 1:
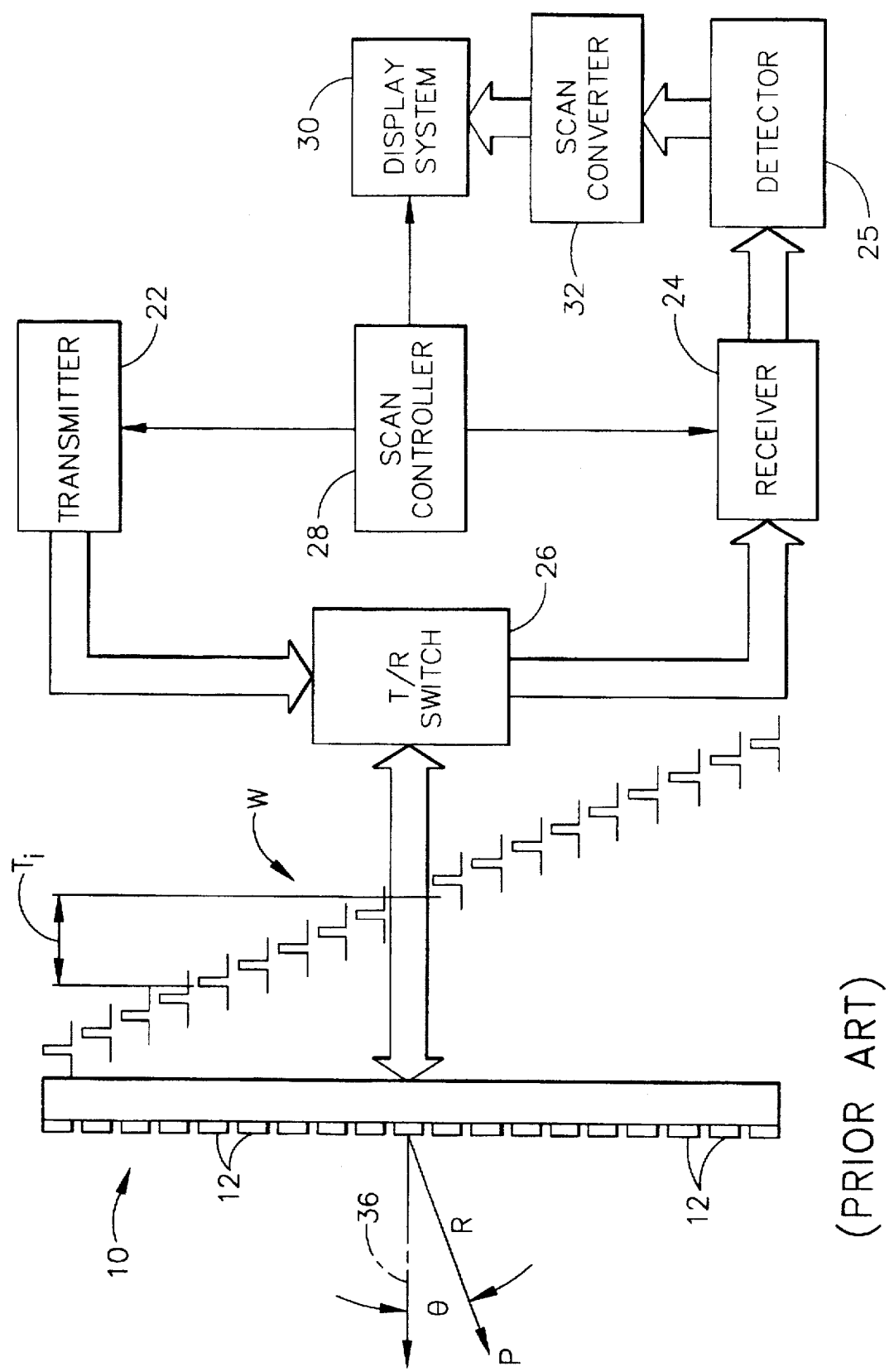
FIG. 1 is a block diagram showing the major functional subsystems within a conventional real-time ultrasound imaging system.
Figure 2:
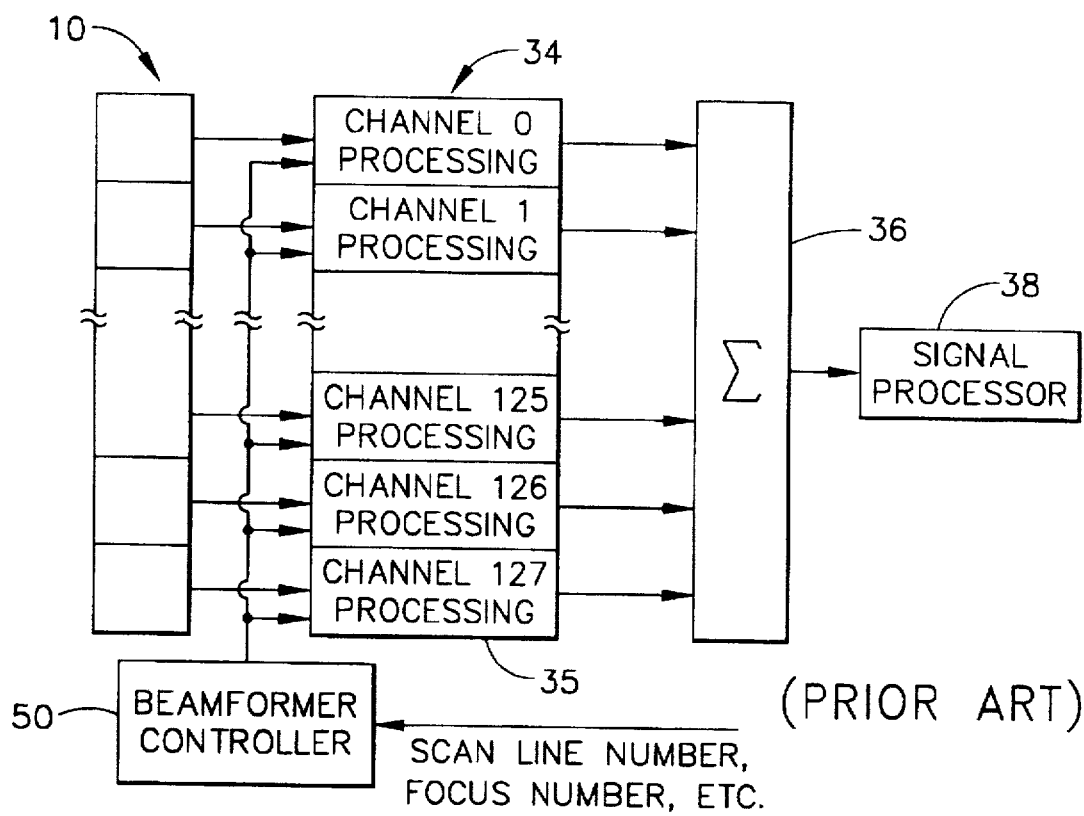
FIG. 2 is a block diagram of a typical 128-channel beamformer for the system depicted in FIG. 2.
Figure 3:
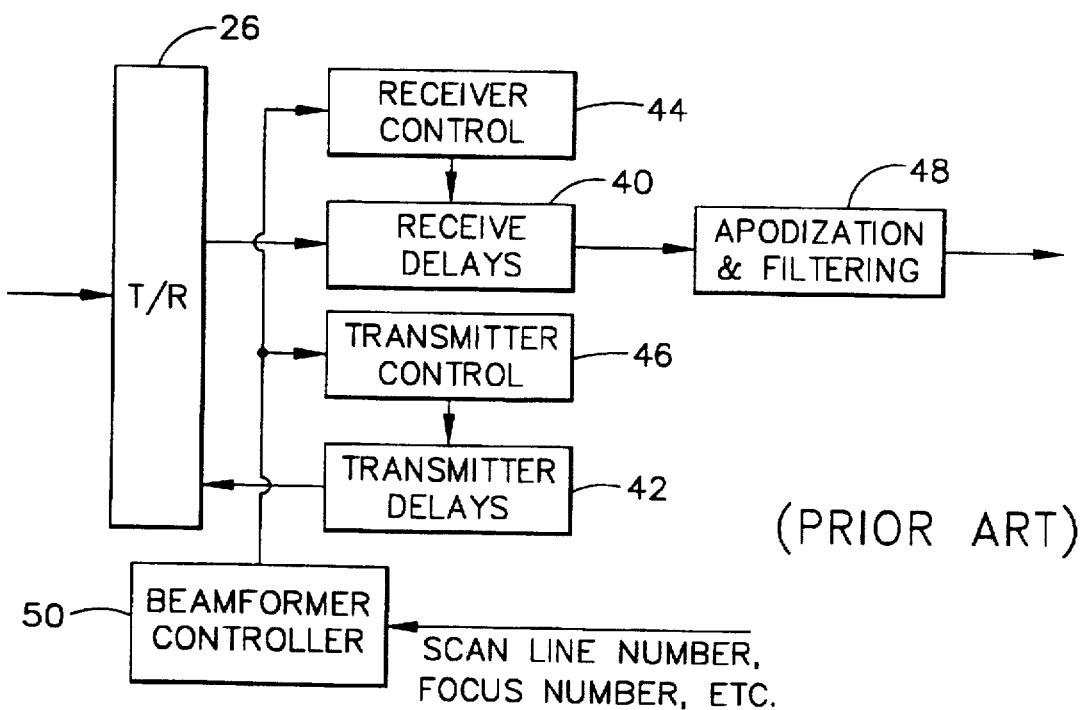
FIG. 3 is a block diagram of the channel processing in the conventional beamformer depicted in FIG. 2.
Figure 2A:
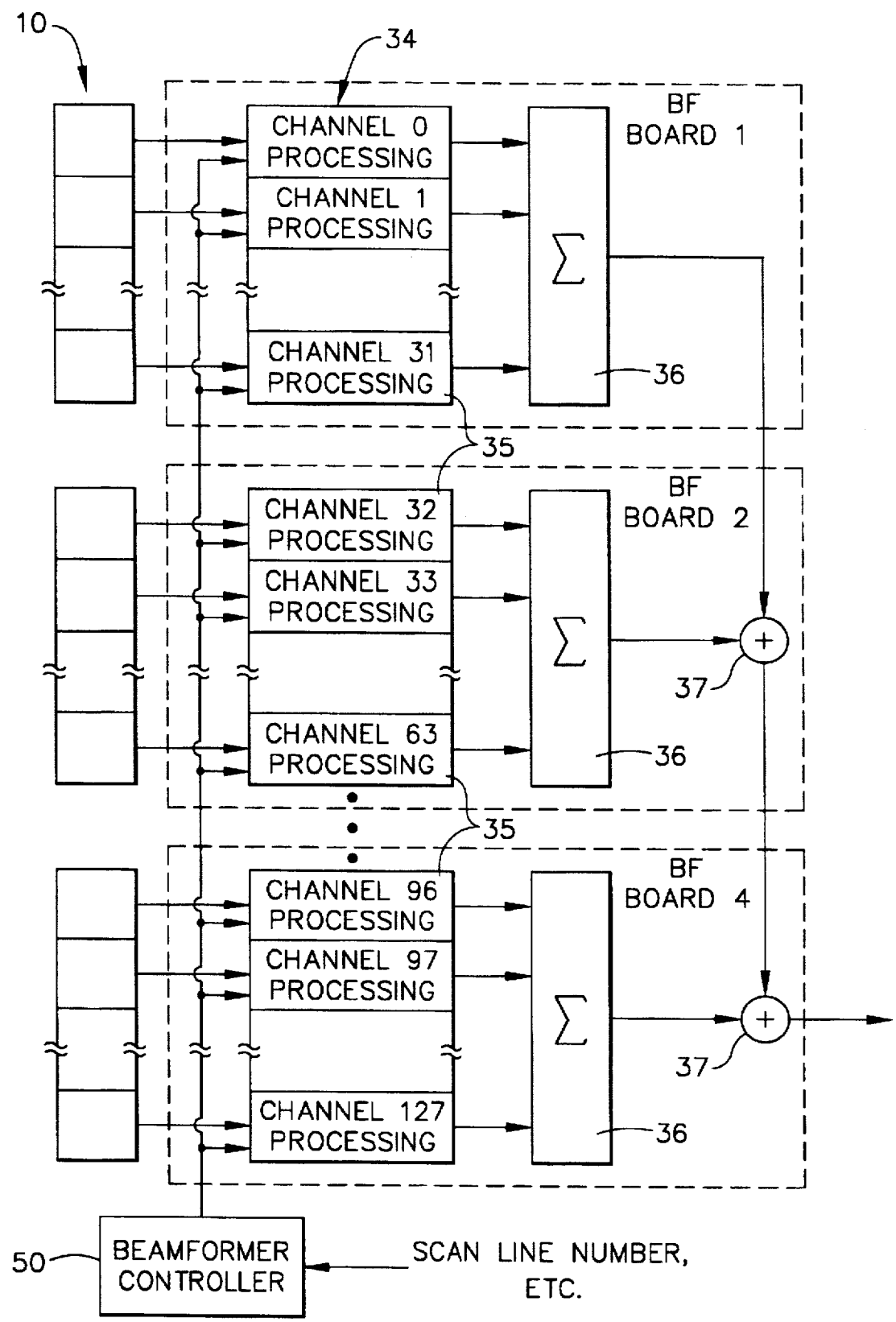
FIG. 2A is a block diagram of a typical 128-channel beamformer arranged on four boards for the system depicted in FIG. 2.
Figure 2B:
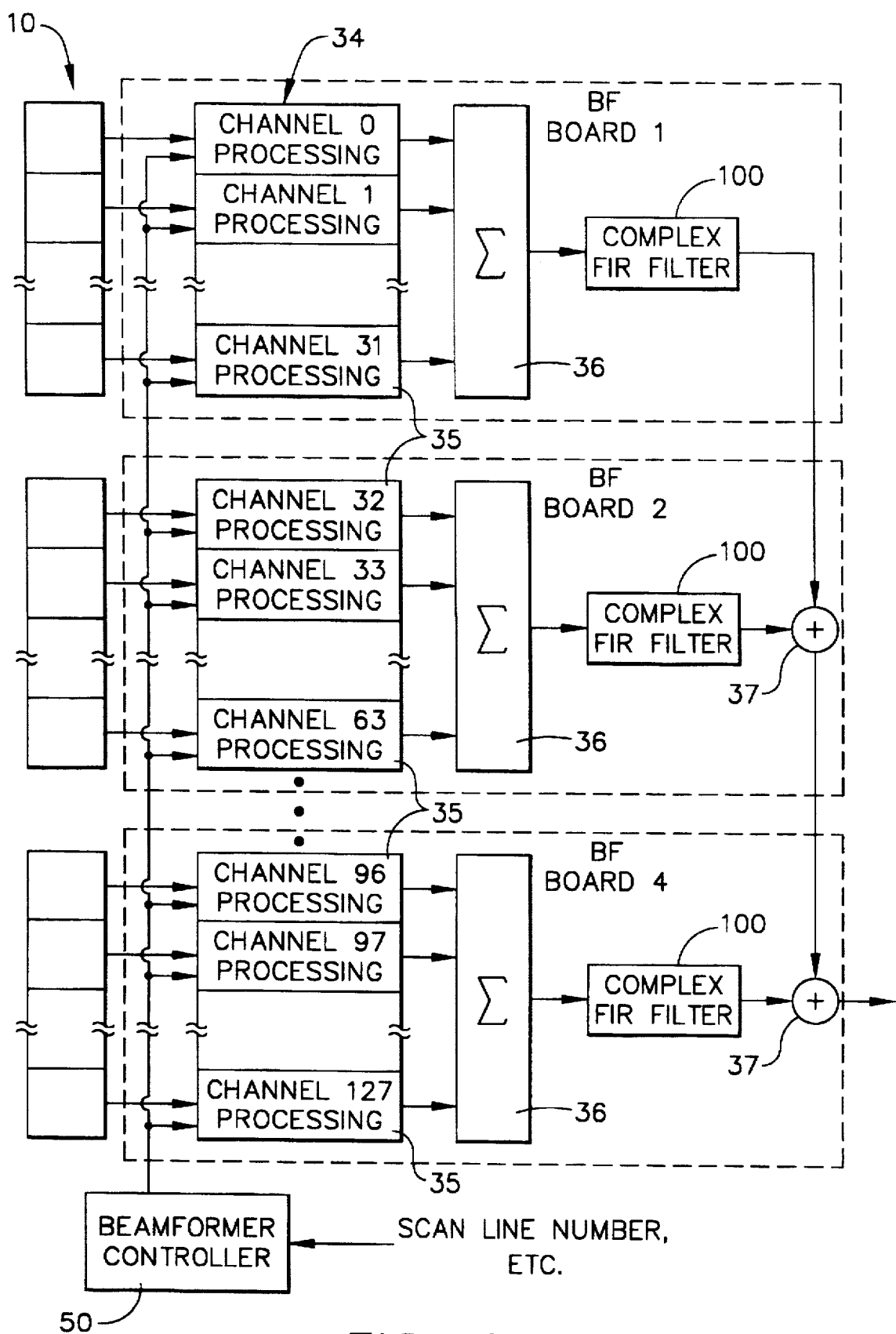
FIG. 2B is a block diagram of a 128-channel beamformer arranged on four boards for an ultrasound imaging system in accordance with the present invention.
Figure 4:
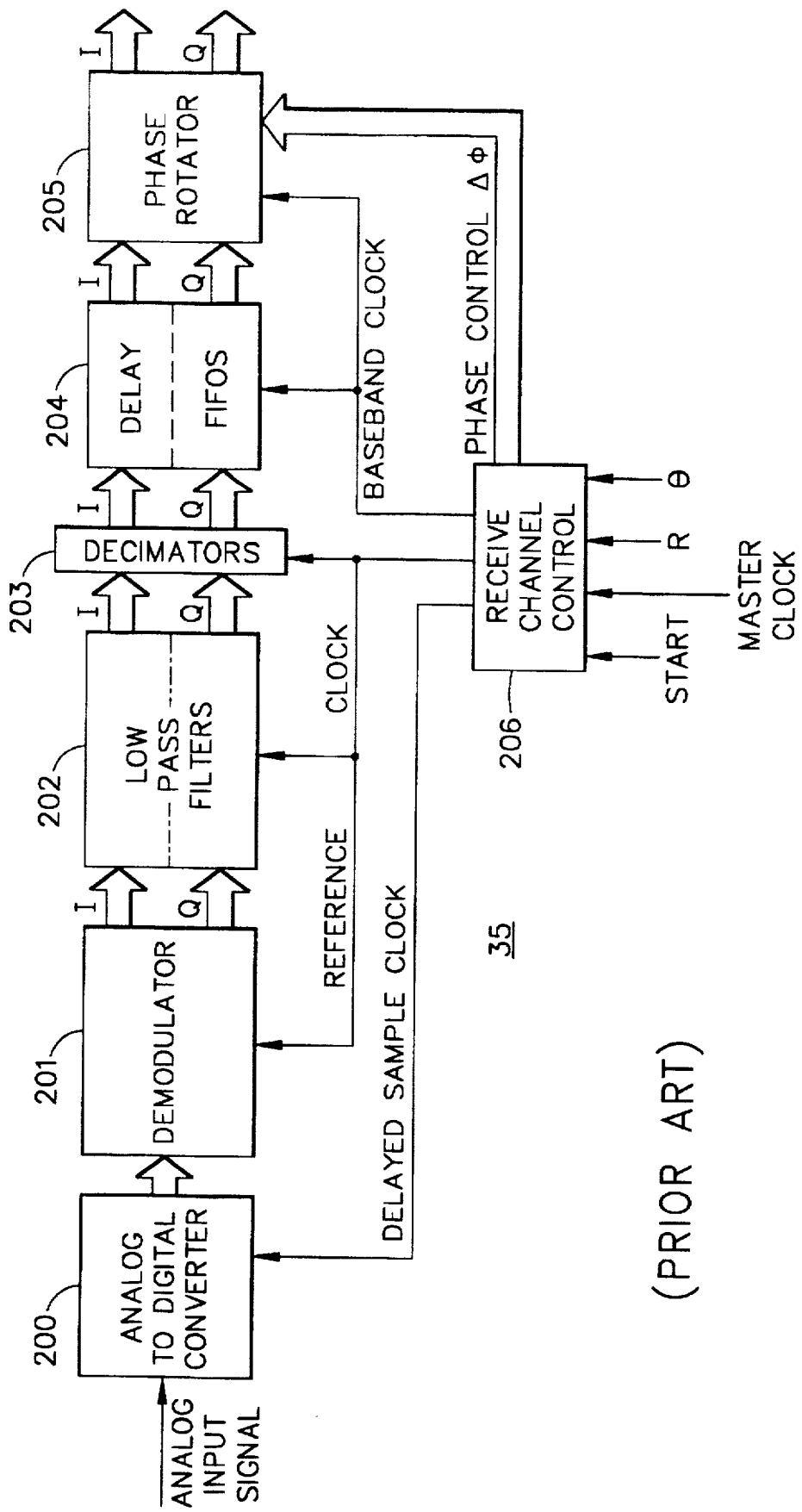
FIG. 4 is a block diagram showing the functional organization of each processing channel depicted in FIG. 3.

In accordance with the present invention generally depicted in FIG. 2B, each beamformer board comprises a multiplicity of processing channels 34 having inputs connected to respective elements of an ultrasound transducer array 10 and having outputs connected to a corresponding multiplicity of inputs of a summer 36. The output of each summer 36 is connected to the input of a respective complex FIR filter circuit 100. After complex bandpass filtering, the filtered signals from the four beamformer boards are added by adders 37, the summed filtered signals then being input to the signal detector (not shown in FIG. 2B).

In accordance with the preferred embodiment of the invention, each complex FIR filter circuit 100 has the organization shown in FIG. 5. This complex bandpass filter provides nondestructive sample rate conversion from the input 40 MHz data rate to 5 or 10 MHz data streams. The complex bandpass filtering circuit 100 comprises three stages 102, 104 and 106. Two configurations are provided. A 10-MHz configuration outputs 10-MHz sampled complex data from the second stage, bypassing the third stage. A 5-MHz configuration outputs 5-MHz sampled complex data from the third stage.

The three-stage complex bandpass filter shown in FIG. 5 removes noise and interference, as well as the undesired sidebands, while allowing subsampling without destructive aliasing. All three stages can be used to produce a 5-MHz output sample rate, or only the first two stages can be used to produce a 10-MHz output rate, depending on the frequency. The filters in accordance with the preferred embodiment of the invention are designed to accommodate greater than 70% fractional bandwidth for B-mode imaging with less than 1 dB amplitude variation. These filters attenuate the negative frequencies more than 45 dB over this bandwidth and 60 dB over a 30% bandwidth. The filters have a typical stop-band of 50 dB with a worst case out-of-band attenuation better than 20 dB.

Each of filter stages 102, 104 and 106 is a FIR filter with 11 taps, only some of which are used. There are less than 7 non-zero coefficients. The coefficients are limited to sums or differences of two powers of 2. The filter coefficients for the first stage 102 are listed in Table 1; the coefficients for the second stage 104 are listed in Table 2; and the coefficients for the third stage are listed in Table 3.

TABLE 1

| Freq. | h(−5) | h(−4) | h(−3) | h(−2) | h(−1) | h(0) | h(1) | h(2) | h(3) | h(4) | h(5) |
|---|---|---|---|---|---|---|---|---|---|---|---|
| 2.5 | 0 | 0 | −9 | 0 | 65 | 112 | 65 | 0 | −9 | 0 | 0 |
| 3.75–5.0 | 0 | 0 | 0 | −14i | 33 − 33i | 66 | 33 + 33i | 14i | 0 | 0 | 0 |
| 6.25 | −2 | 0 | 9i | 0 | 40 | 48 + 48i | 40i | 0 | 9 | 0 | −2i |
| 7.5–10.0 | −2i | 0 | −9i | 0 | −40i | 66 | 40i | 0 | 9i | 0 | 2i |

TABLE 2

| Freq. | h(−5) | h(−4) | h(−3) | h(−2) | h(−1) | h(0) | h(1) | h(2) | h(3) | h(4) | h(5) |
|---|---|---|---|---|---|---|---|---|---|---|---|
| 2.5 | 0 | 0 | 0 | −14i | 33 − 33i | 66 | 33 + 33i | 14i | 0 | 0 | 0 |
| 3.75–6.25 | −2i | 0 | −9i | 0 | −40i | 66 | 40i | 0 | 9i | 0 | 2i |
| 7.5 | −2 | 0 | −9i | 0 | 40 | −48 + 48i | −40i | 0 | 9 | 0 | 2i |
| 10.0 | −2 | 0 | 9 | 0 | −40 | 66 | −40 | 0 | 9 | 0 | −2 |

TABLE 3

| Freq. | h(−5) | h(−4) | h(−3) | h(−2) | h(−1) | h(0) | h(1) | h(2) | h(3) | h(4) | h(5) |
|---|---|---|---|---|---|---|---|---|---|---|---|
| 2.5 | −2i | 0 | −9i | 0 | −40i | 66 | 40i | 0 | 9i | 0 | 2i |
| 3.75 | −2 | 0 | −9i | 0 | 40 | −48 + 48i | −40i | 0 | 9 | 0 | 2i |
| 5.0 | −2 | 0 | 9 | 0 | −40 | 66 | −40 | 0 | 9 | 0 | −2 |

The output of each stage may be selectively complex conjugated to provide additional filtering bands. Complex conjugation is simply sign inversion of the Q data. Complex conjugation before and after a stage of a complex FIR filter flips the FIR frequency response about the Nyquist frequency (½ the input sample rate). For example, a second-stage complex bandpass FIR filter, with an input sample rate of 20 MHz and a passband center frequency of 7.5 MHz, may be flipped around 10 MHz to provide a passband centered at 12.5 MHz. Similarly, a 6.25-MHz center frequency band can be provided, using the 3.75-MHz third-stage coefficients, by complex conjugating the outputs of the second and third stages.

Control for the complex bandpass filters is provided by three two-bit filter select fields, three one-bit complex conjugate selects, and a one-bit configuration control. The two-bit field for each of the three stages will select one of the four filters available. The one bit configuration control selects either the 10-MHz left-only mode or the 5-MHz left/right mode.

Figure 6:
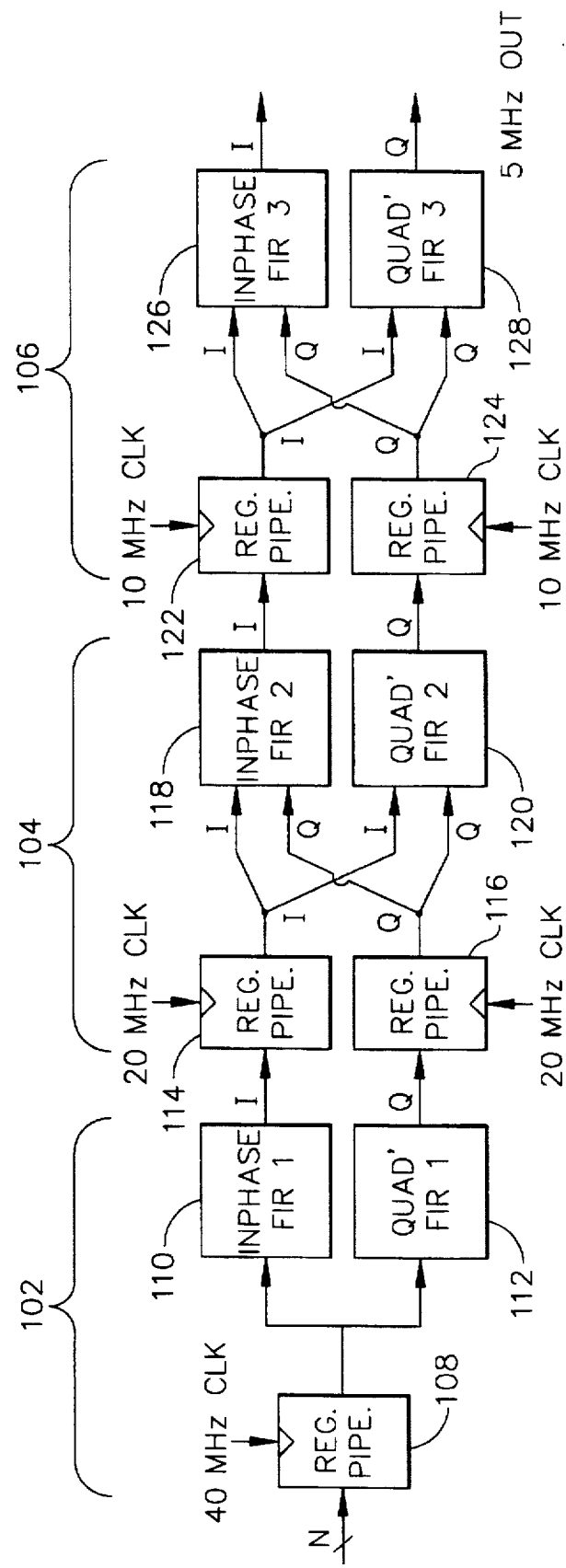
FIG. 6 is a block diagram of a three-stage complex FIR filter circuit in accordance with the preferred embodiment of the invention.
Figure 7:
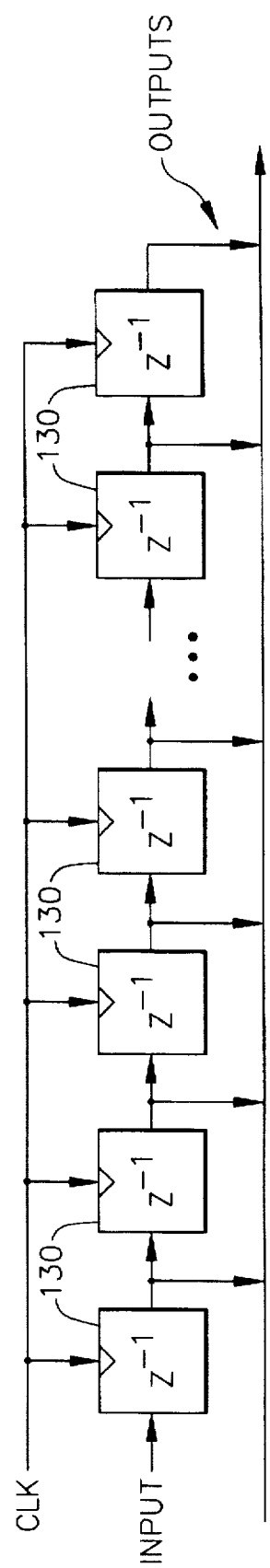
FIG. 7 is block diagram of a register pipeline incorporated in each stage of the complex FIR filter circuit depicted in FIG. 6.

FIG. 6 shows a three-stage complex FIR filter. In accordance with the preferred embodiment of the invention shown in FIG. 6, each of filter circuit stages 102, 104 and 106 comprises a register pipeline (shown in greater detail in FIG. 7), an in-phase FIR filter and a quadrature FIR filter. The first stage only has real samples, so there is a single pipeline. The other stages have complex inputs composed of in-phase (real) and quadrature (imaginary) samples, requiring a pipeline for each. As seen in FIG. 7, each register pipeline comprises a multiplicity of registers 130 connected in series. The designation "z⁻¹" in FIG. 7 signifies a single sample time delay. The number of registers in a given pipeline must equal the number of taps being used on the FIR filter immediately downstream of the register pipeline. The registers 130 are clocked in synchronism and store successive echo data samples. Each register 130 in the pipeline has an output connected to a respective tap of the corresponding FIR filter. In the second and third stages, the taps on FIR filters 118, 120, 126 and 128 receive complex data samples from the I and Q pipelines, each complex data sample consisting of a real data sample from the I pipeline and an imaginary data sample from the Q pipeline. As explained in more detail hereinafter, in the FIR filters for the second and third stages, the complex data sample input to each filter tap is multiplied by a respective filter coefficient and these products are then summed to form the filtered data sample.

In particular, filter circuit stage 102 comprises a register pipeline 108 having an input and a multiplicity of outputs, an in-phase FIR filter 110 having a multiplicity of taps respectively connected to the multiplicity of outputs of register pipeline 108, and a quadrature FIR filter 112 having a multiplicity of taps respectively connected to the multiplicity of outputs of register pipeline 108. The register pipeline 108 is clocked at a rate of 40 MHz. The in-phase FIR filter 110 outputs an in-phase (I) signal, while the quadrature FIR filter 112 outputs a quadrature (Q) signal. Due to the reduction in bandwidth, the output sample rate of the first stage may be reduced by half to 20 MHz.

Still referring to FIG. 6, the output of the in-phase FIR filter 110 is connected to the input of a register pipeline 114, whereas the output of the quadrature FIR filter 112 is connected to the input of a register pipeline 116. Register pipelines 114 and 116 each have a multiplicity of outputs and may be identical in structure to register pipeline 108. The multiplicity of outputs of I data sample register pipeline 114 are respectively connected to a multiplicity of taps of an in-phase FIR filter 118 and to a multiplicity of taps of a quadrature FIR filter 120. Similarly, the multiplicity of outputs of Q data sample register pipeline 116 are respectively connected to the taps of in-phase FIR filter 118 and to the taps of quadrature FIR filter 120. Each register pipeline 114 and 116 is clocked at a rate of 20 MHz. The in-phase FIR filter 118 outputs an in-phase (I) signal, while the quadrature FIR filter 120 outputs a quadrature (Q) signal. Due to the reduction in bandwidth, the output sample rate of the second stage may be reduced by half to 10 MHz.

The output of the in-phase FIR filter 118 is in turn connected to the input of a register pipeline 122; the output of the quadrature FIR filter 120 is connected to the input of a register pipeline 124. Register pipelines 122 and 124 each have a multiplicity of outputs and may again be identical in structure to register pipeline 108. The multiplicity of outputs of I data sample register pipeline 122 are respectively connected to a multiplicity of taps of an in-phase FIR filter 126 and to a multiplicity of taps of a quadrature FIR filter 128. Similarly, the multiplicity of outputs of Q data sample register pipeline 124 are respectively connected to the taps of in-phase FIR filter 126 and to the taps of quadrature FIR filter 128. Each register pipeline 122 and 124 is clocked at a rate of 10 MHz. The in-phase FIR filter 126 outputs an in-phase (I) signal, while the quadrature FIR filter 128 outputs a quadrature (Q) signal.

In accordance with the preferred embodiment of the invention, the input to the first stage is at a 40-MHz sample clock rate. The output of each stage is at half the sample rate of the input. Either two or three stages may be used to produce either 10 MHz or 5 MHz complex outputs. The filter coefficients in accordance with the preferred embodiment produce a 6 dB bandwidth equal to the sample rate.

The coefficients for the in-phase and quadrature FIR filters shown in FIG. 6 are respectively given in Tables 1-3 for the three stages. Each stage has three or four possible coefficient sets. The coefficients are all combination of two powers of 2. Thus, the four (three) sets of coefficients are implemented with four (three) bit shift and add circuits for a given FIR filter. For example, as shown in FIG. 8, the first-stage in-phase FIR filter comprises first through fourth bit shift and add circuits 132A-132D which have been respectively hard-wired to shift and/or invert bits in accordance with the four sets of coefficients in table 1. Each shift and add circuit is connected to receive the data samples input on the filter taps and then multiply the data samples by the respective filter coefficients by bit shifting and adding. Multiplication by −1 is performed by inverting the bits and adding 1. A 4-to-1 multiplexer 134 selects the output of one of the four shift and add circuits 132A-132D. The filter coefficients in accordance with the preferred embodiment have the breakdown given in Table 4.

TABLE 4

| Coefficients | Breakdown |
| --- | --- |
| 2 | 2 |
| 9 | 8 + 1 |
| 14 | 16 − 2 |
| 33 | 32 + 1 |
| 40 | 32 + 8 |
| 48 | 32 + 16 |
| 65 | 64 + 1 |
| 66 | 64 + 2 |

To provide more flexibility, the output of each quadrature FIR may be inverted. For example, as shown in FIG. 9, the first-stage quadrature FIR filter comprises first through fourth bit shift and add circuits 132E-132H which have been respectively hard-wired to shift and/or invert bits in accordance with the four sets of coefficients in table 1. A 4-to-1 multiplexer 136 selects the output of one of the four bit shift and add circuits 132E-132H. The output of multiplexer 136 is inverted by inverter 138 and passed to one input of a 2-to-1 multiplexer 140. This inversion is equivalent to complex conjugation. The other input of multiplexer 140 receives the uninverted output of multiplexer 136.

The complex coefficients listed in Tables 1-3 are broken up into real and imaginary coefficients, which are applied separately to the in-phase and quadrature FIR filters, respectively. For example, the quadrature coefficients (coefficients in Tables 1-3 with "i" next to them) are applied to "I" inputs in the quadrature FIR filter and to "Q" inputs in the in-phase FIR filter (with sign inversion). The in-phase coefficients (without "i"s) are applied to "Q" inputs in the quadrature FIR filter and to "I" inputs in the in-phase FIR filter. [Note, however, that the first stage FIR filters have no "IQ" inputs.] Each of these coefficients is applied to the register pipeline output corresponding to the respective column in Tables 1-3. Each coefficient may be implemented via two hard-wired bit shifts and optional inversions, as generally shown in FIG. 10, in which each bit shift/invert block 142 represents two distinct shift/invert circuits which receive the same input. Two shifted/inverted values per non-zero coefficient are supplied to a Wallace tree adder 144.

An advantage of the foregoing method is that no multipliers are needed; only shifts, inversions and one Wallace tree adder are needed per shift and add block. The bit shifters require no control or active circuitry; the shifts are simply performed by shifting the bit connections. Inversion is very simple, and a Wallace tree adder provides the most efficient, fast method for adding many numbers in a VLSI implementation.

Figure 11A:
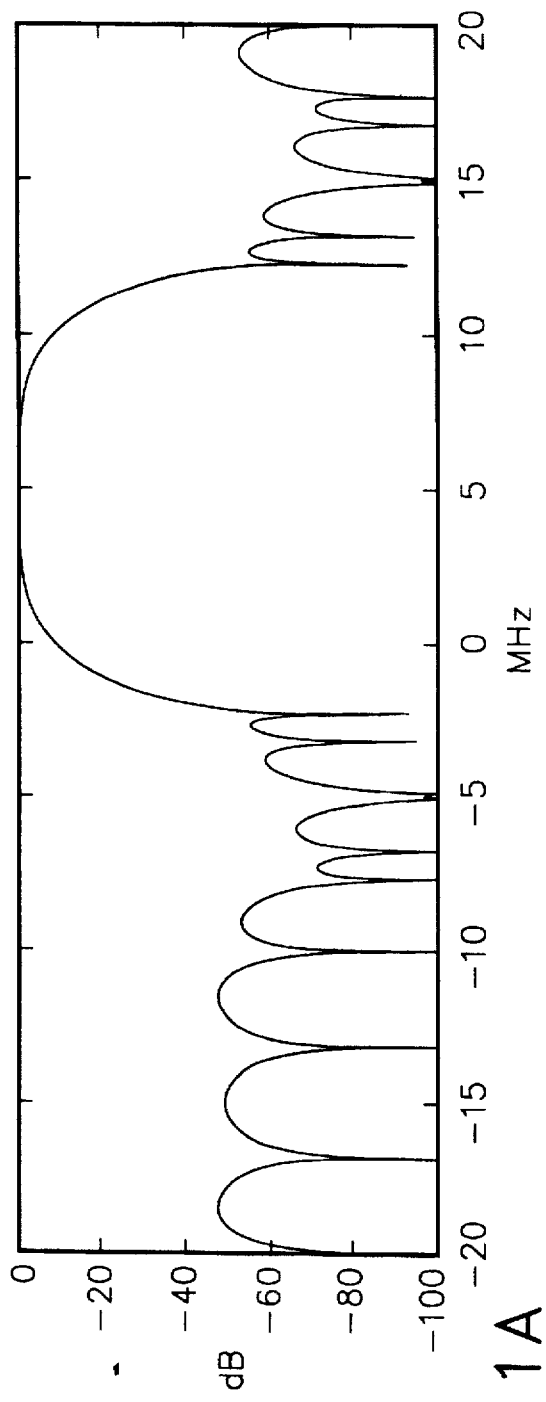
FIGS. 11A and 11B are graphs of output magnitude versus input frequency (solid lines) for a bandpass filter in accordance with the invention having a center frequency of 5.0 MHz sampled at 5 and 10 MHz, respectively.
Figure 11B:
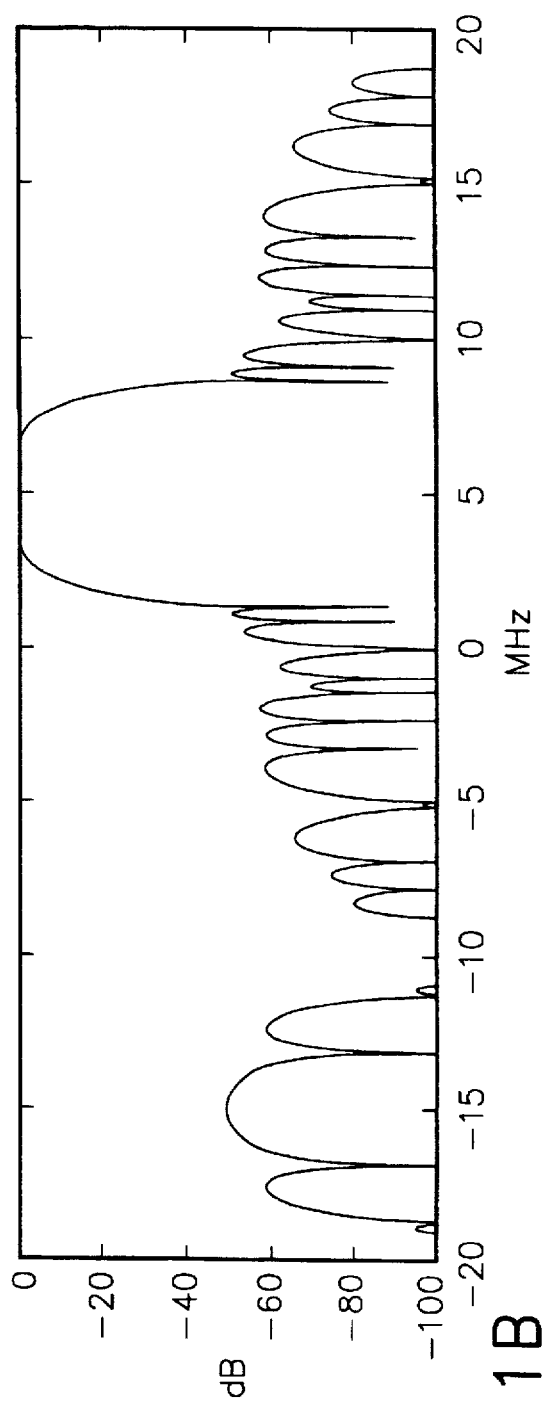

The overall sensitivity functions and passbands of the bandpass filters in accordance with the invention are shown in FIGS. 11A and 11B, which show the relative output magnitude versus input frequency for a center frequency of 5.0 MHz sampled at 5and 10 MHz, respectively.

The foregoing preferred embodiment has been disclosed for the purpose of illustration. Variations and modifications will be readily apparent to those skilled in the art of beamforming for ultrasound imaging. For example, it will be apparent that a separate complex FIR filter can be incorporated in each beamformer channel upstream of the summer, instead of after the summer as disclosed hereinabove. Also, decimation may take place in the FIR filters rather than in the register pipelines, e.g., in the case of decimation by ½, the FIR filters can be operated only during every other sampling period. All such variations and modifications are intended to be encompassed by the claims set forth hereinafter.

We claim:

1. A complex FIR filter circuit comprising:

a first register pipeline clocked at a first sampling rate and having a plurality of outputs for outputting in each sampling period a respective plurality of successive digital samples derived from an input stream of digital samples;

a first filtering means for outputting in at least every other sampling period an in-phase filtered digital sample and a quadrature filtered digital sample derived from said plurality of successive digital samples output by said first register pipeline by applying a first set of complex filter coefficients;

a second register pipeline clocked at a second sampling rate less than said first sampling rate and having a plurality of outputs for outputting in each sampling period a respective plurality of successive digital samples derived from said in-phase filtered digital samples output by said first filtering means;

a third register pipeline clocked at said second sampling rate and having a plurality of outputs for outputting in each sampling period a respective plurality of successive digital samples derived from said quadrature filtered digital samples output by said first filtering means; and a second filtering means for outputting in at least every other sampling period an in-phase filtered digital sample and a quadrature filtered digital sample derived from said plurality of successive digital samples output by said second register pipeline and said plurality of successive digital samples output by said third register pipeline by applying a second set of complex filter coefficients.

2. The complex FIR filter circuit as defined in claim 1, wherein said first filtering means comprise:

first shifting/inverting means for bit shifting and/or inverting said respective plurality of successive digital samples output by said first register pipeline in accordance with a first set of bit shift and/or invert values derived from said first set of complex filter coefficients; and first adding means for adding said shifted/inverted digital samples output by said first shifting means.

3. The complex FIR filter circuit as defined in claim 1, further comprising:

a fourth register pipeline clocked at a third sampling rate less than said second sampling rate and having a plurality of outputs for outputting in each sampling period a respective plurality of successive digital samples derived from said in-phase filtered digital samples output by said second filtering means;

a fifth register pipeline clocked at said third sampling rate and having a plurality of outputs for outputting in each sampling period a respective plurality of successive digital samples derived from said quadrature filtered digital samples output by said second filtering means; and a third filtering means for outputting in at least every other sampling period a respective in-phase filtered digital sample and a respective quadrature filtered digital sample derived from said respective plurality of successive digital samples output by said fourth register pipeline and said respective plurality of successive digital samples output by said fifth register pipeline by applying a third set of complex filter coefficients.

4. The complex FIR filter circuit as defined in claim 1, wherein said first filtering means comprise:

a first in-phase FIR filter for outputting in at least every other sampling period a respective in-phase filtered digital sample derived from said respective plurality of successive digital samples output by said first register pipeline by bit shifting and/or inverting in accordance with a first set of bit shift and/or invert values derived from said first set of complex filter coefficients; and a first quadrature FIR filter for outputting in at least every other sampling period a respective quadrature filtered digital sample derived from said respective plurality of successive digital samples output by said first register pipeline by bit shifting and/or inverting in accordance with a second set of bit shift and/or invert values derived from said first set of complex filter coefficients.

5. The complex FIR filter circuit as defined in claim 2, wherein said first filtering means further comprises:

second shifting/inverting means for bit shifting and/or inverting said respective plurality of successive digital samples output by said first register pipeline in accordance with a second set of bit shift and/or invert values derived from said first set of complex filter coefficients;

second adding means for adding said shifted/inverted digital samples output by said second shifting means; and a multiplexer having first and second inputs coupled to receive outputs from said first and second adding means respectively.

6. The complex FIR filter circuit as defined in claim 2, wherein said second filtering means comprise:

second shifting/inverting means for bit shifting and/or inverting said respective plurality of successive digital samples output by said second and third register pipelines in accordance with second and third sets of bit shift and/or invert values derived from said second set of complex filter coefficients; and second adding means for adding said shifted/inverted digital samples output by said second shifting means.

7. The complex FIR filter circuit as defined in claim 2, wherein said first adding means comprises a Wallace tree adder.

8. The complex FIR filter circuit as defined in claim 4, wherein said second filtering means comprise:

a second in-phase FIR filter for outputting in at least every other sampling period a respective in-phase filtered digital sample derived from said respective plurality of successive digital samples output by said second register pipeline and said respective plurality of successive digital samples output by said third register pipeline by bit shifting and/or inverting in accordance with a third set of bit shift and/or invert values derived from said second set of complex filter coefficients; and a second quadrature FIR filter for outputting in at least every other sampling period a respective quadrature filtered digital sample derived from said respective plurality of successive digital samples output by said second register pipeline and said respective plurality of successive digital samples output by said third register pipeline by bit shifting and/or inverting in accordance with a fourth set of bit shift and/or invert values derived from said second set of complex filter coefficients.

9. A beamformer comprising a multiplicity of beamformer channels, a summer having a multiplicity of inputs respectively coupled to said multiplicity of beamformer channels, and a complex FIR filter circuit having an input connected to an output of said summer, wherein said complex FIR filter circuit comprises:

a first register pipeline clocked at a first sampling rate and having a plurality of outputs for outputting in each sampling period a respective plurality of successive digital samples derived from an input stream of digital samples;

a first filtering means for outputting in at least every other sampling period an in-phase filtered digital sample and a quadrature filtered digital sample derived from said plurality of successive digital samples output by said first register pipeline by applying a first set of complex filter coefficients;

a second register pipeline clocked at a second sampling rate less than said first sampling rate and having a plurality of outputs for outputting in each sampling period a respective plurality of successive digital samples derived from said in-phase filtered digital samples output by said first filtering means;

a third register pipeline clocked at said second sampling rate and having a plurality of outputs for outputting in each sampling period a respective plurality of successive digital samples derived from said quadrature filtered digital samples output by said first filtering means; and a second filtering means for outputting in at least every other sampling period an in-phase filtered digital sample and a quadrature filtered digital sample derived from said plurality of successive digital samples output by said second register pipeline and said plurality of successive digital samples output by said third register pipeline by applying a second set of complex filter coefficients.

10. The beamformer as defined in claim 9, wherein said first filtering means comprise:

first shifting/inverting means for bit shifting and/or inverting said respective plurality of successive digital samples output by said first register pipeline in accordance with a first set of bit shift and/or invert values derived from said first set of complex filter coefficients; and first adding means for adding said shifted/inverted digital samples output by said first shifting means.

11. The beamformer as defined in claim 9, further comprising:

a fourth register pipeline clocked at a third sampling rate less than said second sampling rate and having a plurality of outputs for outputting in each sampling period a respective plurality of successive digital samples derived from said in-phase filtered digital samples output by said second filtering means;

a fifth register pipeline clocked at said third sampling rate and having a plurality of outputs for outputting in each sampling period a respective plurality of successive digital samples derived from said quadrature filtered digital samples output by said second filtering means; and a third filtering means for outputting in at least every other sampling period a respective in-phase filtered digital sample and a respective quadrature filtered digital sample derived from said respective plurality of successive digital samples output by said fourth register pipeline and said respective plurality of successive digital samples output by said fifth register pipeline by applying a third set of complex filter coefficients.

12. The beamformer as defined in claim 9, wherein said first filtering means comprise:

a first in-phase FIR filter for outputting in at least every other sampling period a respective in-phase filtered digital sample derived from said respective plurality of successive digital samples output by said first register pipeline by bit shifting and/or inverting in accordance with a first set of bit shift and/or invert values derived from said first set of complex filter coefficients; and a first quadrature FIR filter for outputting in at least every other sampling period a respective quadrature filtered digital sample derived from said respective plurality of successive digital samples output by said first register pipeline by bit shifting and/or inverting in accordance with a second set of bit shift and/or invert values derived from said first set of complex filter coefficients.

13. The beamformer as defined in claim 10, wherein said first filtering means further comprises:

second shifting/inverting means for bit shifting and/or inverting said respective plurality of successive digital samples output by said first register pipeline in accordance with a second set of bit shift and/or invert values derived from said first set of complex filter coefficients;

second adding means for adding said shifted/inverted digital samples output by said second shifting means; and a multiplexer having first and second inputs coupled to receive outputs from said first and second adding means respectively.

14. The beamformer as defined in claim 10, wherein said second filtering means comprise:

second shifting/inverting means for bit shifting and/or inverting said respective plurality of successive digital samples output by said second and third register pipelines in accordance with second and third sets of bit shift and/or invert values derived from said second set of complex filter coefficients; and second adding means for adding said shifted/inverted digital samples output by said second shifting means.

15. The beamformer as defined in claim 10, wherein said first adding means comprises a Wallace tree adder.

16. The beamformer as defined in claim 12, wherein said second filtering means comprise:

a second in-phase FIR filter for outputting in at least every other sampling period a respective in-phase filtered digital sample derived from said respective plurality of successive digital samples output by said second register pipeline and said respective plurality of successive digital samples output by said third register pipeline by bit shifting and/or inverting in accordance with a third set of bit shift and/or invert values derived from said second set of complex filter coefficients; and a second quadrature FIR filter for outputting in at least every other sampling period a respective quadrature filtered digital sample derived from said respective plurality of successive digital samples output by said second register pipeline and said respective plurality of successive digital samples output by said third register pipeline by bit shifting and/or inverting in accordance with a fourth set of bit shift and/or invert values derived from said second set of complex filter coefficients.

17. An ultrasonic imaging system comprising a transducer array, a beamformer coupled to said transducer array, a signal processor coupled to said beamformer, a scan converter coupled to said signal processor, and a display monitor coupled to said scan converter, wherein said transducer array comprises a multiplicity of transducer elements and said beamformer comprises a multiplicity of beamformer channels, switching circuitry for selectively coupling said beamformer channels to said transducer elements, summing means having a multiplicity of inputs respectively coupled to said multiplicity of beamformer channels, and a complex FIR filter circuit having an input connected to an output of said summer, wherein said complex FIR filter circuit comprises:

a first register pipeline clocked at a first sampling rate and having a plurality of outputs for outputting in each sampling period a respective plurality of successive digital samples derived from an input stream of digital samples;

a first filtering means for outputting in at least every other sampling period an in-phase filtered digital sample and a quadrature filtered digital sample derived from said plurality of successive digital samples output by said first register pipeline by applying a first set of complex filter coefficients;

a second register pipeline clocked at a second sampling rate less than said first sampling rate and having a plurality of outputs for outputting in each sampling period a respective plurality of successive digital samples derived from said in-phase filtered digital samples output by said first filtering means;

a third register pipeline clocked at said second sampling rate and having a plurality of outputs for outputting in each sampling period a respective plurality of successive digital samples derived from said quadrature filtered digital samples output by said first filtering means; and a second filtering means for outputting in at least every other sampling period an in-phase filtered digital sample and a quadrature filtered digital sample derived from said plurality of successive digital samples output by said second register pipeline and said plurality of successive digital samples output by said third register pipeline by applying a second set of complex filter coefficients.

18. The ultrasonic imaging system as defined in claim 17, wherein said first filtering means comprise:

first shifting means for bit shifting and/or inverting said respective plurality of successive digital samples output by said first register pipeline in accordance with a set of bit shift and/or invert values derived from said first set of complex filter coefficients; and first adding means for adding said shifted/inverted digital samples output by said second shifting means.

19. The ultrasonic imaging system as defined in claim 17, wherein said complex FIR filter circuit further comprises:

a fourth register pipeline clocked at a third sampling rate less than said second sampling rate and having a plurality of outputs for outputting in each sampling period a respective plurality of successive digital samples derived from said in-phase filtered digital samples output by said second filtering means;

a fifth register pipeline clocked at said third sampling rate and having a plurality of outputs for outputting in each sampling period a respective plurality of successive digital samples derived from said quadrature filtered digital samples output by said second filtering means; and a third filtering means for outputting in at least every other sampling period a respective in-phase filtered digital sample and a respective quadrature filtered digital sample derived from said respective plurality of successive digital samples output by said fourth register pipeline and said respective plurality of successive digital samples output by said fifth register pipeline by applying a third set of complex filter coefficients.

20. A method of downsampling digital samples in an ultrasound beamformer, comprising the steps of:

acquiring a stream of digital data samples;

clocking said digital data samples in succession through a first register pipeline at a first sampling rate, said first register pipeline storing a respective multiplicity of digital data samples during each successive sampling period, each multiplicity of digital data samples being output in parallel in response to a respective clock signal output at said first sampling rate;

bit shifting and/or inverting each multiplicity of digital data samples in accordance with a first set of bit shift and/or invert values derived from a first set of complex filter coefficients to produce a first multiplicity of filtered digital data samples;

bit shifting and/or inverting each multiplicity of digital data samples in accordance with a second set of bit shift and/or invert values derived from said first set of complex filter coefficients to produce a second multiplicity of filtered digital data samples;

adding said respective first multiplicity of bit shifted/inverted digital data samples to produce a respective first-stage in-phase digital data sample;

adding said respective second multiplicity of bit shifted/inverted digital data samples to produce a respective first-stage quadrature digital data sample;

clocking said respective first-stage in-phase digital data samples in succession through a second register pipeline at a second sampling rate less than said first sampling rate, said second register pipeline storing a respective multiplicity of in-phase digital data samples during each successive sampling period, each multiplicity of in-phase digital data samples being output in parallel in response to a respective clock signal output at said second sampling rate;

clocking said respective first-stage quadrature digital data samples in succession through a third register pipeline at said second sampling rate, said second register pipeline storing a respective multiplicity of quadrature digital data samples during each successive sampling period, each multiplicity of quadrature digital data samples being output in parallel in response to said respective clock signal output at said second sampling rate;

bit shifting and/or inverting each multiplicity of in-phase digital data samples from said second register pipeline and each multiplicity of quadrature digital data samples from said third register pipeline in accordance with a third set of bit shift and/or invert values derived from a second set of complex filter coefficients to produce a third multiplicity of filtered digital data samples;

bit shifting and/or inverting each multiplicity of in-phase digital data samples from said second register pipeline and each multiplicity of quadrature digital data samples from said third register pipeline in accordance with a fourth set of bit shift and/or invert values derived from said second set of complex filter coefficients to produce a fourth multiplicity of filtered digital data samples;

adding said respective third multiplicity of bit shifted/ inverted digital data samples to produce a respective second-stage in-phase digital data sample; and adding said respective fourth multiplicity of bit shifted/ inverted digital data samples to produce a respective second-stage quadrature digital data sample.

* * * * *